United States Patent
Lieberman et al.

(10) Patent No.: US 6,726,655 B1
(45) Date of Patent: *Apr. 27, 2004

(54) MEDICATION DELIVERY SYSTEM

(75) Inventors: Marc S. Lieberman, Poway, CA (US); Michael W. Kleeman, Sudbury, MA (US); David R. Brengle, San Diego, CA (US)

(73) Assignee: Tandem Medical, Encinitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/434,972

(22) Filed: Nov. 5, 1999

(51) Int. Cl.[7] .......................... A61M 37/00; A61M 5/00
(52) U.S. Cl. ....................... 604/131; 604/191
(58) Field of Search .................. 604/65, 66, 67, 604/131, 134, 135, 141, 151, 191, 27; 128/DIG. 12, DIG. 13

(56) References Cited

U.S. PATENT DOCUMENTS

| | | | |
|---|---|---|---|
| 2,124,907 A | 7/1938 | Bunting | 221/60 |
| 2,168,080 A | 8/1939 | Allen | 221/60 |
| 2,461,891 A | 2/1949 | Giles | 222/101 |
| 2,742,189 A | 4/1956 | Morrison | 222/100 |
| 3,198,385 A | 8/1965 | Maxwell | 222/41 |
| 3,469,578 A | 9/1969 | Bierman | 128/214 |
| 3,543,966 A | 12/1970 | Ryan et al. | 222/94 |
| 3,640,277 A | 2/1972 | Adelberg | 128/214 F |
| 3,647,117 A | 3/1972 | Hargest | 222/100 |
| 3,670,926 A | 6/1972 | Hill | 222/47 |
| 4,019,655 A | 4/1977 | Moeller | 222/96 |
| 4,258,864 A | 3/1981 | Karamanolis et al. | 222/96 |
| 4,337,769 A | 7/1982 | Olson | 128/214 |
| 4,364,474 A | 12/1982 | Hollander, Jr. | 206/219 |
| 4,399,103 A | 8/1983 | Ferrara | 422/100 |
| 4,504,267 A | 3/1985 | Parmelee et al. | 604/134 |
| 4,507,114 A | 3/1985 | Bohman et al. | 604/111 |
| 4,512,764 A | 4/1985 | Wunsch | 604/80 |
| 4,522,622 A | 6/1985 | Peery et al. | 604/191 |
| 4,525,164 A | 6/1985 | Loeb et al. | 604/131 |
| 4,557,728 A | 12/1985 | Sealfon et al. | 604/134 |
| 4,559,036 A | 12/1985 | Wunsch | 604/81 |
| 4,576,314 A | 3/1986 | Elias et al. | 222/97 |
| 4,576,603 A | 3/1986 | Moss | 604/410 |
| 4,626,243 A | 12/1986 | Singh et al. | 604/141 |
| 4,666,430 A | 5/1987 | Brown et al. | 604/141 |
| 4,667,854 A | 5/1987 | McDermott et al. | 222/101 |
| 4,731,058 A | 3/1988 | Doan | 604/155 |
| 4,741,736 A * | 5/1988 | Brown | 604/134 |
| 4,753,371 A | 6/1988 | Michielin et al. | 222/144.5 |
| 4,765,512 A | 8/1988 | Bull, Jr. | 222/100 |
| 4,772,263 A | 9/1988 | Dorman et al. | 604/132 |
| 4,784,157 A | 11/1988 | Halls et al. | 128/762 |
| 4,795,441 A | 1/1989 | Bhatt | 604/124 |

(List continued on next page.)

FOREIGN PATENT DOCUMENTS

| | | | |
|---|---|---|---|
| EP | 0 145 825 | 6/1985 | A61J/1/00 |
| EP | 0145825 * | 6/1985 | A61J/1/00 |
| EP | 0 790 051 A2 | 8/1997 | A61J/1/10 |

OTHER PUBLICATIONS

I–Flow VIVUS 50 and VIVUS 100, Data Sheets, 5 pages, Jun. 1993.

Primary Examiner—Brian L. Casler
Assistant Examiner—Matthew DeSanto
(74) Attorney, Agent, or Firm—Foley & Lardner; Stephen E. Reiter (57) ABSTRACT

The present invention comprises a medication delivery system for administering an infusion therapy using a medication delivery pump and related fluid container. Medications in a flexible bag of the container are expelled from the bag by the pump into an administration set and delivered to an infusion site. The administration set limits the rate at which a spring compresses the bag. The system provides improved infusion therapy administration which is particularly advantageous for reducing errors, infections and other complications associated with manual infusion techniques.

31 Claims, 6 Drawing Sheets

U.S. PATENT DOCUMENTS

| | | | |
|---|---|---|---|
| 4,823,833 A | 4/1989 | Hogan et al. | 137/567 |
| 4,830,510 A | 5/1989 | Bellhouse | 366/219 |
| 4,842,576 A | 6/1989 | Lysaght et al. | 604/6 |
| 4,846,637 A | 7/1989 | Alderson et al. | 417/479 |
| 4,850,725 A | 7/1989 | Walker et al. | 400/236.2 |
| 4,850,971 A | 7/1989 | Colvin | 604/134 |
| 4,857,055 A | 8/1989 | Wang | 604/133 |
| 4,898,583 A | 2/1990 | Borsanyi et al. | 604/153 |
| 4,915,688 A | 4/1990 | Bischof | 604/83 |
| 4,957,436 A | 9/1990 | Ryder | 433/88 |
| 4,966,579 A | 10/1990 | Polaschegg | 604/65 |
| 4,997,083 A | 3/1991 | Loretti et al. | 206/219 |
| 5,048,725 A | 9/1991 | Peterson | 222/100 |
| 5,080,652 A | 1/1992 | Sancoff et al. | 604/132 |
| 5,105,983 A | 4/1992 | Sancoff et al. | 222/103 |
| 5,118,011 A | 6/1992 | Kopp | 222/102 |
| 5,176,634 A | 1/1993 | Smith et al. | 604/87 |
| 5,199,604 A | 4/1993 | Palmer et al. | 222/25 |
| 5,205,820 A | 4/1993 | Kriesel | 604/85 |
| 5,207,645 A | 5/1993 | Ross et al. | 604/141 |
| 5,211,626 A | 5/1993 | Frank et al. | 604/65 |
| 5,219,331 A | 6/1993 | Vanderveen | 604/81 |
| 5,308,334 A | 5/1994 | Sancoff | 604/131 |
| 5,308,335 A | 5/1994 | Ross et al. | 604/141 |
| 5,318,515 A | 6/1994 | Wilk | 604/30 |
| 5,330,431 A | 7/1994 | Herskowitz | 604/153 |
| 5,342,313 A | 8/1994 | Campbell et al. | 604/153 |
| 5,368,570 A | 11/1994 | Thompson et al. | 604/131 |
| 5,377,871 A | 1/1995 | Banks et al. | 222/41 |
| 5,394,907 A | 3/1995 | Hjertman et al. | 141/1 |
| 5,411,490 A | 5/1995 | Tennican et al. | 604/236 |
| 5,431,496 A | 7/1995 | Balteau et al. | 383/38 |
| 5,433,704 A | 7/1995 | Ross et al. | 604/67 |
| 5,492,533 A | 2/1996 | Kriesel | 604/132 |
| 5,505,708 A | 4/1996 | Atkinson | 604/140 |
| 5,509,898 A | 4/1996 | Isono et al. | 604/87 |
| 5,560,518 A | 10/1996 | Catterall et al. | 222/99 |
| 5,578,001 A | 11/1996 | Shah | 604/31 |
| 5,578,005 A | 11/1996 | Sancoff et al. | 604/82 |
| 5,628,429 A | 5/1997 | Usen et al. | 222/1 |
| 5,692,645 A | 12/1997 | Ryu | 222/101 |
| 5,775,540 A | 7/1998 | Greenberg | 222/102 |
| 5,853,388 A | 12/1998 | Semel | 604/82 |
| 5,954,696 A * | 9/1999 | Ryan | 604/141 |
| 6,074,366 A * | 6/2000 | Rogers et al. | 604/151 |
| 6,428,518 B1 * | 8/2002 | Brengle et al. | 604/191 |

* cited by examiner

MEDICATION DELIVERY SYSTEM

FIELD OF THE INVENTION

The present invention generally relates to system for the intravenous infusion of medication in accordance with a predetermined medical therapy. Medication delivery systems are provided which are useful for improving the ease of administration therapy.

BACKGROUND OF THE INVENTION

Intravenous medications including antibiotics and the like may be administered intermittently over a period of time. Each administration of an intravenous therapy generally follows a predefined procedure that often includes a series of manual steps including saline flushes and generally terminates with the application of anti-clotting medication. The manual steps in the therapy procedures are a principle source of error, infection, and other complications that may arise during intermittent infusion therapy.

Accordingly, there is still a need in the art for systems which improve the administration of intermittent medication infusion therapy. The present invention satisfies this and other needs in the art.

BRIEF DESCRIPTION OF THE INVENTION

The present invention overcomes many of the problems in the art by providing a medication delivery system for administering an infusion therapy using a mechanical medication delivery pump and related fluid container. Medications in a flexible multi-chambered bag of the container are expelled from the bag by the pump into an administration set and delivered to an infusion site. The administration set may further comprise a restrictor which limits the rate at which fluid is administered to the patient. The system provides improved infusion therapy administration which is particularly advantageous for reducing errors, infections and other complications associated with manual infusion techniques.

In one embodiment of the invention, the medication delivery system includes a bag having at least one chamber containing a medication fluid; a pump having a constant force spring for compressing the bag to generate a predetermined pressure in the chamber based on the chamber's configuration, and an administration set. The administration set receives the medication fluid from the bag at the predetermined pressure and delivers the medication fluid to an infusion site at a predetermined flow rate. The administration set may include a micro-bore tubing having a length and an inner diameter that establishes the predetermined flow rate. The administration set also may include an air-eliminating filter for eliminating air bubbles from the medication fluid before delivery of the fluid to the infusion site.

The medication delivery system may further include a manifold between the bag and the administration set. The manifold may include at least one check valve associated with a respective chamber of the bag. By introducing fluid into the administration set under sufficient pressure and maintaining it there (e.g., by use of a clamp on the tubing of the administration set), a hydraulic lock may be formed that holds the check valve(s) closed and prevents unintentional flow from the bag during handling. The hydraulic lock may be overcome upon the application of a threshold pressure on the chamber (i.e., at least the cracking pressure of the check valve).

Another embodiment of the invention resides in a method for filling a fluid delivery bag having a plurality of chambers. A first predetermined fluid volume is measured and at least one chamber is constrained to a second predetermined volume. The plurality of chambers are filled through a shared bulk fill port with the first predetermined volume of fluid such that a constrained chamber is filled with the second predetermined volume of fluid and remaining chamber(s) is/are filled with a predetermined volume of fluid determined by the first predetermined volume of fluid minus the fluid of the constrained chamber (and the volume of any intervening chambers).

DETAILED DESCRIPTION OF THE INVENTION

In accordance with the present invention, there is provided a medication delivery system for administering an infusion therapy to a patient. The medication delivery system infuses predetermined volumes of intravenous solutions. The medication delivery system provides a simple, easy-to-use system for reducing the number of supplies and the number of labor steps typically used to administer multiple intravenous solutions in the proper volumes and in the proper sequence with minimal user interaction.

Figure 1:
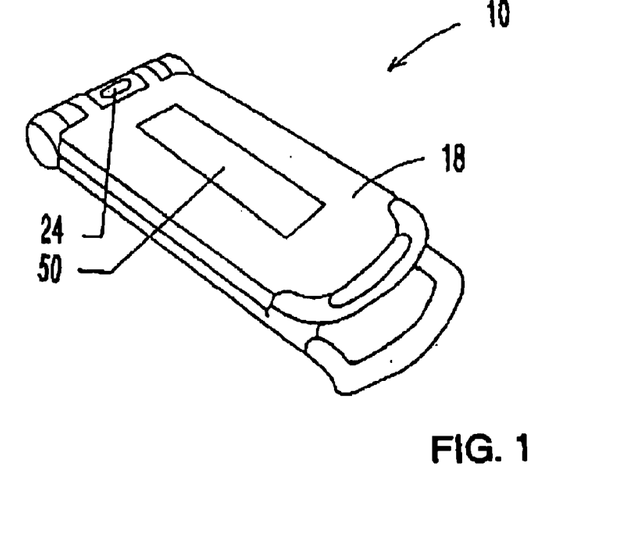
FIG. 1 is a perspective view of a medication delivery pump for use in the medication delivery system of the invention.
Figure 2:
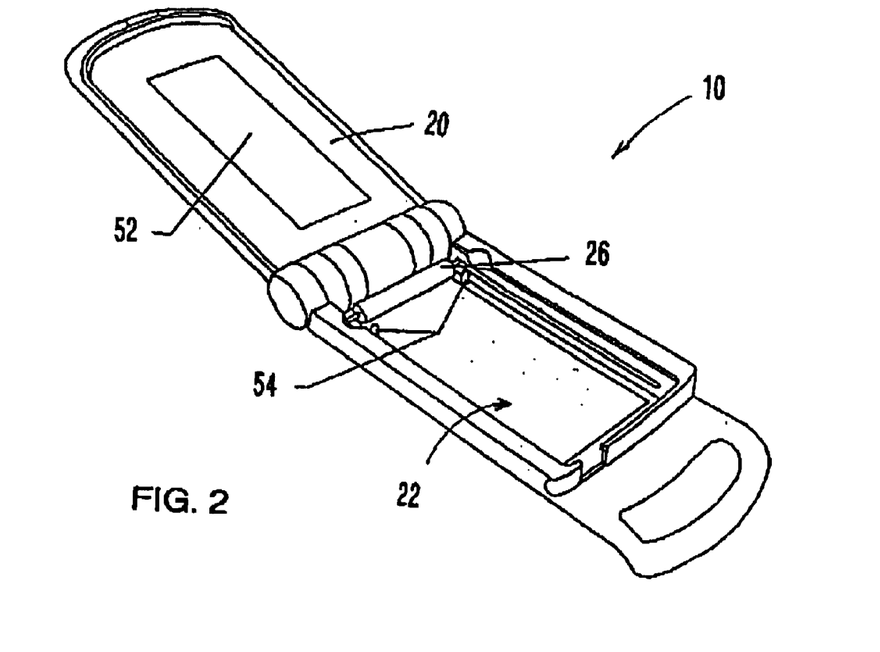
FIG. 2 is a perspective view of the medication delivery pump of FIG. 1, with the pump's cover doors in a fully opened position.
Figure 3:
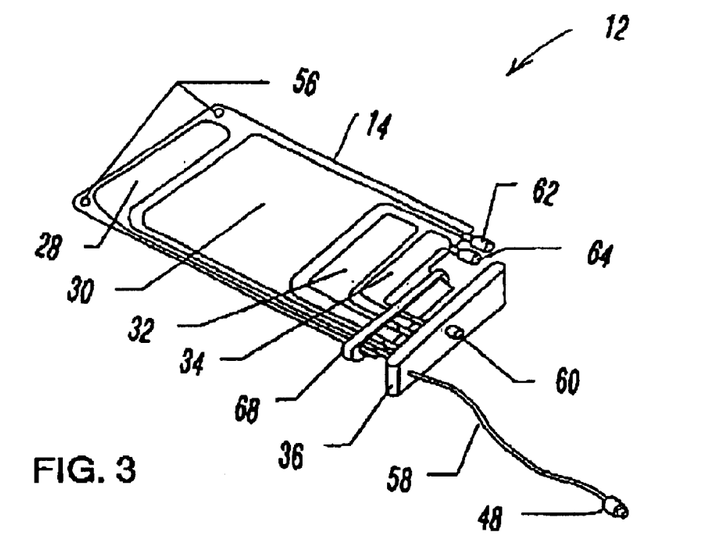
FIG. 3 is a perspective view of a medication delivery bag and manifold for use in the medication delivery system of the invention.

The medication delivery system generally includes three main components: (1) a reusable mechanical pump 10, (2) a sterile, single-use medication delivery container 12 that includes a multi-chamber bag 14 and a sterile, single use administration set 16, and (3) optionally, a reusable filling fixture. Examples of embodiments of the pump, container and administration set are provided in FIGS. 1–3 as discussed below.

Containers (i.e., "bags") contemplated for use in the practice of the present invention comprise a plurality of chambers, each configured to hold a predetermined volume of fluid, and each placed in relation to the others in a manner that determines the order in which the fluids contained therein are administered. Each chamber has an associated exit conduit whereby fluid can exit each chamber for administration to a patient. Thus, for example, a container might have four separate chambers, each sized to hold a different amount of fluid. The container can be filled so that each chamber has a different medication therein. If the four chambers are arranged sequentially in the bag from one end of the bag to the other, and each chamber is activated sequentially from one end of the bag to the other, then fluid will be driven out of the first chamber, and then the second, and so on until each chamber has been emptied.

Each chamber may further comprise an associated filling conduit for introduction of fluids into the chamber. Or a conduit associated with each chamber may be a dual purpose exit/fill conduit. Containers may be filled in a variety of ways by a pharmacist or like technician. Similarly, the container may be provided to a pharmacist in a variety of states. For example, the bag may be provided filled, or empty for subsequent sterilization and filling at the pharmacy. It is presently preferred that the multi-chambered bag is provided sterile and is then filled at the pharmacy. The bag may be appropriately filled using standard pharmaceutical admixture procedures and equipment. Each chamber may be manually filled using injection ports or the like. Alternatively each chamber can be filled by introduction of fluids into a common filling conduit that branches off to the respective fill or dual purpose fill/exit conduit associated with each chamber. Once the bag is prepared, it is labeled and sent from the pharmacy to the end user.

In another embodiment of the present invention, containers further comprise a manifold to provide fluid communication to the administration set, and to regulate delivery of the medication from the bag port of the conduits to an administration set, and also optionally provides a structure for filling the container. As used herein, "bag port of the conduit" and "bag port" refer to the terminal portion of each conduit leading to/from a chamber in the bag. The bag ports may have an adapter affixed thereto for mating the bag ports with the manifold, or the manifold may be attached directly to the bag ports. The manifold can be any structure that is attachable to the bag ports (or adapters) in a fluid-tight manner while providing a common outlet for all bag ports to the administration set. Thus, the manifold will comprise structures corresponding to the bag ports for connection thereto.

Manifolds contemplated for use in the practice of the present invention will have manifold conduits for directing fluid from chamber ports to the output port, and then to the administration set, and from the bulk fill port, when employed, to the chamber ports. These manifold conduits can be isolated from one another in a fluid-tight manner and can comprise internally molded chambers connecting the desired portions of the manifold, or they may comprise internally mounted tubing connecting the appropriate portions of the manifold, combinations thereof, or the like.

It is presently preferred that the system be completely mechanical in operation so that the patient need not rely on electrical power for the correct administration of fluids. Accordingly, in one embodiment of the present invention the chambers can be activated by sequential application of pressure. This can be accomplished by placing the container in a pump that sequentially applies pressure via a mechanical mechanism such as a constant force spring, a roller driven by a constant force spring, or the like. By using a constant force spring, or equivalent force applying structure, the rate at which pressure is applied from one end of the bag to the other is relatively steady.

Because the rate at which pressure is applied from one end of the bag to the other is relatively steady, if a pause between the administration of fluids from adjacent chambers is desired (e.g., to prevent mixing of their contents during administration), a space can be provided between the adjacent chambers. In this manner, fluid is driven out of the first of the adjacent chambers, and pressure is applied to the system for a time sufficient to allow the first chamber fluid to substantially clear the bag before the second chamber is encountered by the pump and activated. The size of the space between adjacent chambers determines the relative duration of the pause between the adjacent chambers.

In one embodiment of the present invention, there is provided a filling fixture. The filling fixture facilitates correct filling of the bag and secures the bag during the filling process. In one aspect of this embodiment, the filling fixture comprises a structure sized to receive and contain a bag. The filling fixture is further sized to physically limit the amount of fluid that can be introduced into any one chamber. This is accomplished, for example, by calibrating the structure to prevent expansion of a bag contained in the structure beyond a set volume. Bags contemplated for use in the practice of the present invention, as further detailed below, are essentially two dimensional prior to filling. The chambers of the bag are similarly two dimensional, and are bounded on four sides (considering the associated conduit(s) as essentially dead-end streets) so that expansion in those four directions is not possible. Expansion into the third dimension is the only way for a chamber (and the bag itself) to accommodate increasing volumes of fluid. Thus the filling fixture physically constrains the bag in the third dimension, thereby limiting the volume of fluid that each chamber can accommodate. Accordingly, the operator places the empty container in the fixture and introduces liquid into each chamber until it is filled. By providing a standard sized filling fixture, bags can be provided with chambers sized to accept a predetermined volume of fluid given the constraints to be provided by the filling fixture.

In one embodiment the filling fixture comprises a box with a removable wall (i.e., a door) for introduction and removal of the bag. The removable wall is securable when it is in place. Any device(s) may be employed for securing the removable wall including hinges, latches, and the like, and combinations of two or more thereof. In additional embodiments, the fixture further comprises fold-out legs on one end, in this manner, the fixture can be laid flat for use or it may be stood on end by deploying the fold-out legs.

The order in which chambers are filled can be predetermined by employing one or more check valves in the filling fixture. The valve is positioned on a wall of the fixture so that it bears down on a conduit (hereinafter a "restricted conduit") associated with a chamber that is to be filled last. Fluid introduced into the bag will preferentially seek chambers associated with conduits that are not impinged upon by a valve, until the fluid in the chambers being filled exert sufficient back pressure on the restricted conduit so as to lift the check valve and allow fluid flow into the associated chamber. Any number of check valves may be employed. Moreover, the cracking pressure of each valve need not be the same, thereby allowing for further control over the order in which chambers are filled.

In another embodiment, the filling fixture is configured to include structure that operates to automatically open a shipping clamp on the bag when the bag is inserted into the fixture, or when the door is closed on the fixture. Similarly, the filling fixture may operate to automatically close the shipping clamp when the bag is filled, or alternatively when the bag is removed from the fixture.

The pump contemplated for use in the practice of the present invention comprises a mechanism for activating ("activating mechanism") multi-chambered bags as described herein. The pump comprises a housing for retaining a bag in operative relationship to the activating mechanism. As used herein, "operative relationship" means that the activating mechanism and bag are positioned relative to one another so that the activating mechanism can sequentially activate the chambers in the bag. The activating mechanism can be a constant force spring, as further described herein, or the like. It is presently preferred that the pump housing comprise structure to facilitate orientation of the bag securely in operative relationship with the activating mechanism. Contemplated structures for this purpose include positioning pins that match holes in a medication container bag, fasteners (e.g., hook and loop, snaps, buttons, zippers, or the like) that mate with counterparts on the bag, or the like. In a particular embodiment, the housing is further configured to receive a manifold attached to the bag. By employing sufficient structure to retain the manifold, orientation of the bag securely in operative relationship with the activating mechanism is further facilitated.

The housing also comprises structure for receiving and securing the activating mechanism. Because the pump is preferentially completely mechanical, it is simplest if the activating mechanism applies force in a constant manner. Accordingly, it may be desirable to govern the rate at which the activating mechanism operates on the bag. Thus, in another embodiment, the pump further comprises a governing mechanism (hereinafter "energy absorption device") which is connected to and receives energy from the activating mechanism. The energy is dissipated in a manner that controls the rate by which the activating mechanism can apply force to the bag. Any suitable energy absorption device may be employed. Energy absorption devices contemplated for use in the practice of the present invention include watch-type gear assemblies (as further described herein), and the like. Alternatively, if the system is configured to be electrically powered, then the force and rate of force application can be governed electronically by any suitable means.

The pump will further comprise a charging mechanism for charging the activating mechanism. Thus, the user can install the bag in the pump housing and cock or charge the activating mechanism. Accordingly, in an embodiment where a constant force spring is employed, the charging mechanism will act to translate energy input by the user into stored energy in the constant force spring. This can be accomplished in a variety of ways depending on the exact type of constant force spring employed. Because the constant force spring can be a coiled leaf of metal or other suitable material attached to a hub at the center of the coil, in one embodiment the charging mechanism will be attached to the hub. The other end of the spring is fixed to the pump housing proximal to one end of the housing. In this manner, force can be applied to the center of the hub and directed away from the fixed end of the spring, thereby causing the spring to unroll. It is presently preferred that the hub of the spring protrude from either side of the spring so that the hub can be captured in a track or like structure for retaining and guiding the travel of the constant force spring. In this manner, the travel of the spring can be controlled during charging and in performing its work. It is especially preferred that the hub have additional structure for facilitating even retraction of the spring (i.e., so that one side is not unrolled faster than the other). This can be accomplished in a variety of ways including employing a toothed gear and track assembly, as further described herein, or the like. The hub, gear and track assembly serves an additional function of providing an attachment point for the energy absorption device described herein, as well as a means to control the forward (i.e., work producing) travel of the spring.

Charging mechanisms contemplated for use in the practice of the present invention include a force transmission structure suitable for pushing or pulling the hub of the spring in the intended direction (i.e., away from the fixed end of the spring). Suitable force transmission structures include chains, belts, rods or the like, if the hub is to be pulled; and rods, or the like if the hub is to be pushed. It is presently preferred that the force transmission structure be connected to a mechanism for providing a mechanical advantage to the user, as the energy required to charge the constant force spring can be substantial. A mechanical advantage can be provided in the form of a lever mechanism, a multi-stage cocking mechanism, or the like. The multi-stage cocking mechanism allows partial cocking or charging of the constant force spring during each stage of the cocking. In this manner, the often substantial force required to charge the constant force spring can be parceled out over several operation stages, thereby making cocking easier than if a single stage mechanism where employed.

In a further embodiment of the present invention, there are provided methods for infusing a subject with medication, wherein the method comprises employing the system described herein in any one or more of its embodiments.

The invention will now be described in greater detail by reference to specific, non-limiting embodiments. Moreover, each of the embodiments of the various components described below need not necessarily be used in conjunction with the other specific embodiments shown.

Figure 4:
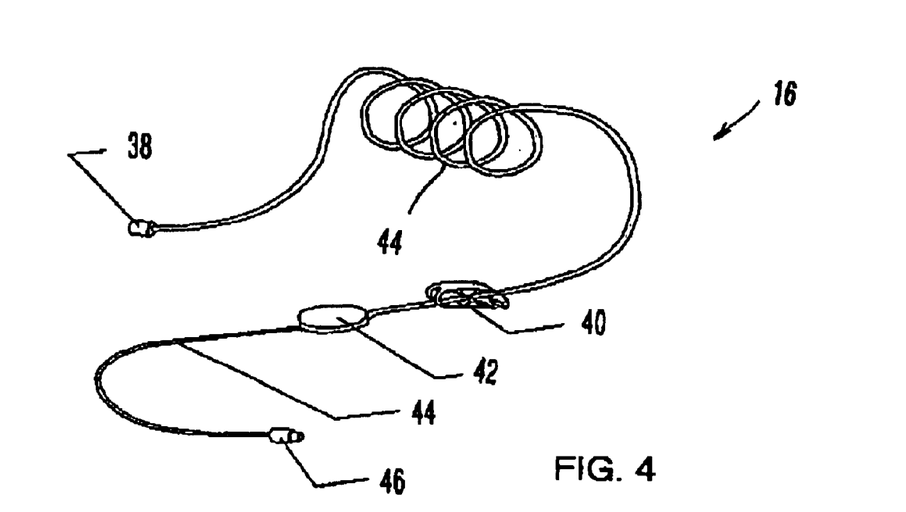
FIG. 4 is a schematic view of an administration set for use in the medication delivery system of the invention.
Figure 5:
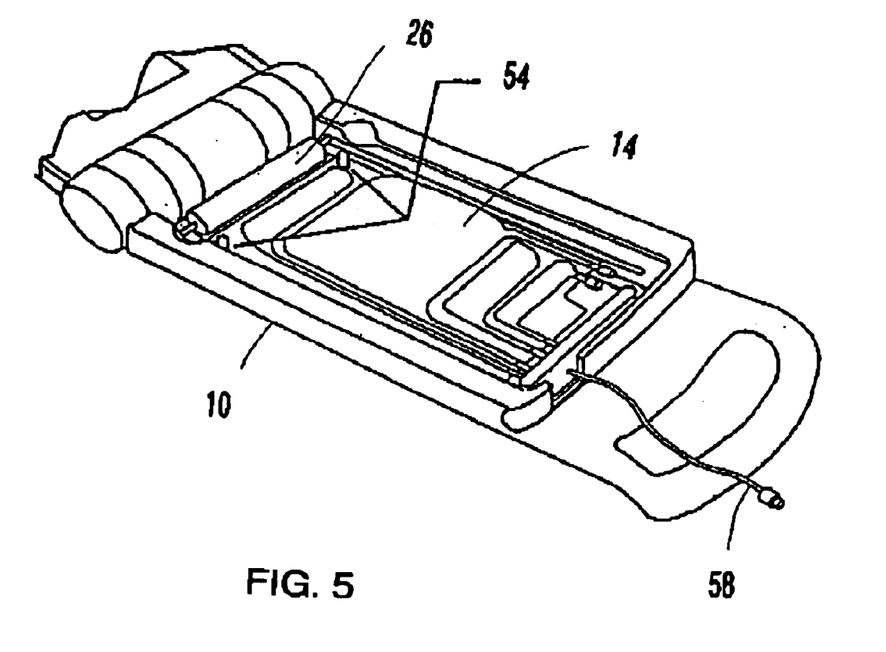
FIG. 5 is a perspective view of the medication delivery bag of FIG. 3, placed in a receptacle of the medication delivery pump of FIGS. 1 and 2.

In accordance with a specific embodiment of the invention, the user attaches the administration set 16 to the bag 14 (FIG. 4), opens two doors, 18 and 20, of the pump 10 (FIGS. 1 and 2), thereby charging the activation mechanism, and places the bag inside a receptacle 22 of the pump (FIG. 5). The user then closes the pump's doors, attaches the administration set to a patient's intravenous (i.v.) catheter site, and starts the activation mechanism, for example, by pushing a start button 24. A mechanical spring 26 (e.g., a constant force spring) within the pump compresses each of the bag's four chambers 28, 30, 32 and 34. The respective fluid within each chamber is sequentially expressed out of the bag, through the administration set, and into the patient. In a preferred embodiment, an indicator notifies the user when the infusion is complete. The indicator may be visual, audible, (e.g., a bell, or the like), tactile, or the like.

The medication delivery system is designed to be simple, safe, intuitive, and cost effective. Further, the system is designed to (1) reduce the need for supplies, (2) diminish manual manipulations and labor complexity, (3) decrease entries into the patient's IV catheter, and (4) ensure fluids will be administered in the proper volumes and in the proper sequence.

The medication delivery pump 10 is a mechanical device which does not require electrical energy nor software to infuse the solutions in the correct volume, order, and flow rate. An activating mechanism such as a constant force stainless steel spring 26 provides the mechanical energy to express the fluids as it compresses each solution chamber of the bag 14.

The solution pressures and infusion rates are determined by the system's configuration. A governing mechanism in the pump works to limit the maximum allowable speed of advance of the spring. When the rate of travel of the constant force spring exceeds the maximum rate allowed by the governor, the governor absorbs some of the spring energy to limit the speed of the spring's travel. The governor allows the spring to move over the entire distance of the pump 10 at a minimum, predetermined amount of time. Thus, the pump generates predictable fluid pressures based on the volume of solution in each chamber. Using the predictable fluid pressures, the flow rate from the bag may be selectable using administration sets having predetermined tubing lengths and inner diameters. The continuous force by the spring on the bag, in combination with check valves in a manifold 36 of the container 12, prevents the reverse flow of fluids from the administration set to the container.

Figure 8:
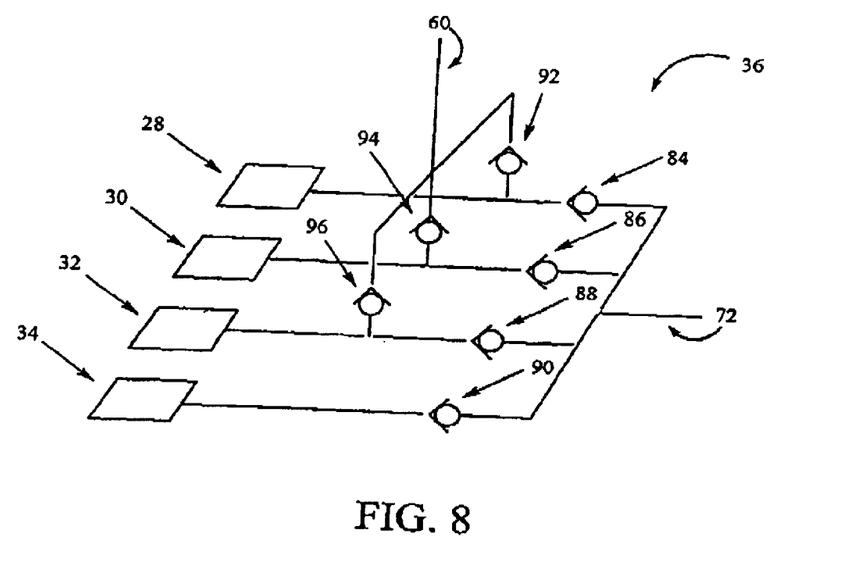
FIG. 8 is a schematic view showing the internal conduit and valve configuration of a manifold assembly for use in the present invention.

An exemplary flow path through a manifold assembly is shown schematically in FIG. 8. The manifold assembly 36 has a tube or output port 72, a bulk fill port 60, and four chamber ports connecting to chambers 28, 30, 32, and 34. Seven check valves, 84, 86, 88, 90, 92, 94, and 96, control the fluid flow direction within the manifold. The manifold assembly may have additional or fewer check valves and ports based on the number and configuration of chambers implemented by the multi-chamber bag.

The administration set, shown in FIG. 4, may include male and female luer connectors (38 and 46, respectively), or other equivalent attachment structures, a tubing clamp 40, an air-eliminating filter 42, a particulate filter (not shown), micro-bore tubing 46, and a flow restrictor (not shown). The tubing of the administration set may be composed of any biocompatible material such as a non-phthalate containing polyvinyl chloride (PVC) (i.e. non-DOP, dioctyl phthalate and non-DEHP, di-2-ethyl-hexylphthalate), or like tubing material which is commonly used in commercially available devices. The administration set may be connected to the bag by means of a standard male luer connector 48 on the bag that couples to the female luer connector of the administration set. The use of standard luer connectors provides assurance that the connection will be achieved easily and correctly. The air eliminating filter removes particulates larger than about 0.2 micron in diameter, and expels air in the fluid stream out of the air vent.

The flow rate through the administration set is selected by varying the microbore tubing's inner diameter and length. The relationship is approximated by Poiseulle's equation:

$$Q = \frac{\Delta p \cdot \pi \cdot D^4}{128 \cdot \mu \cdot L} \qquad \text{Equation 1}$$

Where Q is the flow rate, Δp is the pressure drop across a flow controlling orifice, D is the inside diameter of the orifice, μ is the dynamic viscosity of the fluid and L is the length of the orifice.

In the embodiment where the pump comprises a two stage charging mechanism comprising inner and outer doors, the pump's outer door 18 and inner door 20 must be opened in order to place a filled bag 14 inside the pump 10. The opening motion of the outer door and inner door is the mechanism by which the spring 26 is pulled back to the start position. After the inner door and outer door are closed, the pump is ready to be started upon pushing of the "start" button. It is presently preferred that the system include an interlock mechanism so that activation of the start button can not be accomplished unless both the inner door and outer door are in their closed position.

The pump 10 is depicted with a cut out window 50 in the outer door 18 and a see through window 52 in the inner door 20. These windows allow the user to observe the position of the spring in relation to the bag 14. Accordingly, the user is able to visually monitor the progress of the infusion.

The pump 10 may be designed to separate the bag compartment or receptacle 22 from most of the pump's moving parts. Corrosion resistant materials may be used for any parts that may come in contact with liquids. This attention to the physical design facilitates cleaning of the pump.

The bag 14 may be constructed of an EVA (ethylene vinyl acetate) or like film material which is often used in the construction of intravenous solution containers. This material is generally rugged, durable and biocompatible. The bag is configured to withstand pressures greater than those achieved during an infusion. The pump's bag receptacle 22 is configured such that a filled bag will be positioned correctly and securely. In the depicted embodiment, this is accomplished by the use of registration pins 54 (or similar features) in the pump receptacle to engage, for example, corresponding holes 56 in the bag (See FIG. 5).

Figure 6:
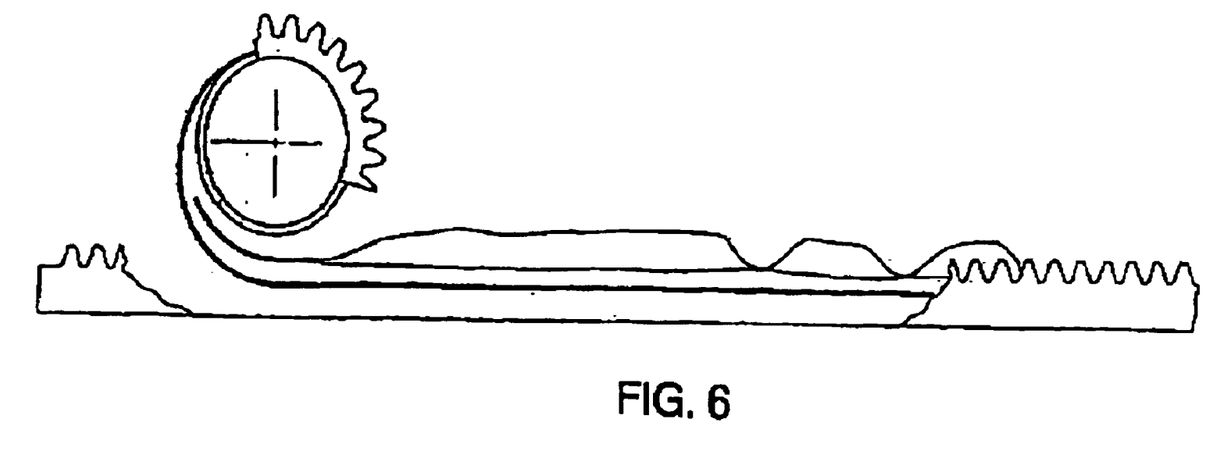
FIG. 6 is a schematic view of a spring assembly of the medication delivery pump, rolling up and compressing the medication delivery bag.

The flow of solution from each chamber is initiated due to a pressure build up caused by the spring 26 compressing the filled chamber (See FIG. 6). As the pressure increases, a check valve in the manifold 36 opens allowing the fluid to flow from the chamber, down a fluid conduit, past the valve, and out through a single outlet tubing 58. When the solution is expelled from the chamber, a drop of pressure occurs which allows the valve to close. It is the opening and closing of the valves that governs the starting and stopping of solution flow from each respective chamber. The controlled rate at which the spring compresses the bag maintains the solution pressure below the typical maximum safe pressure for i.v. devices (i.e., catheters, luers, needles, and the like).

The depicted bag 14 has a fill port 60 for bulk filling chambers 1, 2, and 3 (reference numbers 28, 30 and 34, respectively). The system also has two separate injection sites, 62 and 64, for chambers 2 (30) and 4 (34), respectively, to allow one to add additional solutions.

The administration set 16 may be primed by filling the manifold 36 and the tubing 44 through the bulk fill port 60 while the clamp 40 is locked until the air in the tubing is eliminated through the air-elimination filter 42. Further, a hydraulic lock feature may be formed between the air filter and the check valves by filling the manifold assembly and the tube to a positive pressure great enough to prevent the valves from opening and allowing leakage from the chambers during storage, handling, or transport of the bag 14. The hydraulic lock may be overcome upon the application of a threshold pressure to the respective chambers or release of the pressure by opening the clamp.

The bag 14 may include a shipping clamp 68 for preventing the leakage of any solutions subsequent to filling. When the bag is inserted in the filling fixture, the clamp is released to allow filling. Conversely, when filling is completed, the shipping clamp is closed and prevents leakage of solution from the filled bag prior to use.

The filling fixture (not shown) is a pharmacy tool used only in filling chambers 1, 2 and 3 of the bag. The filling fixture provides a physical constraint to the bag 14 to assure that chambers 1, 2 and 3 are filled to the correct nominal fill volume. This is accomplished by restraining chambers 1 and 3 with the interior walls of the filling fixture.

The operator places the bag 14 into the filling fixture prior to initiating the fill. Once the bag is in the filling fixture, the shipping clamp on the bag, if provided, is opened and the operator bulk fills chambers 1, 2 and 3 of the bag through the bulk fill port 60 in one step, using standard pharmacy filling equipment and procedures.

For example, the operator may fill the bag 14 with 10 mls in chambers 1 and 3, and 100 mls in chamber 2, by setting the standard pharmacy filling equipment to dispense 120 ml. The fluid will flow into the bag filling chambers 1 and 3 to 10 mls. The filling fixture will constrain chambers 1 and 3 to this volume and the remainder of the fluid (100 mls) will flow into chamber 2. When the bag chambers 1, 2 and 3 are filled to the desired volume, the operator removes the bag from the filling fixture. The bag is now ready to have solution added to chambers 2 and 4 via the injection sites, 62 and 64, respectively, as required by the operator. The chamber 2 and chamber 4 injection sites are accessed via standard pharmacy filling equipment and procedures. Upon completion of filling, the bag is ready for insertion into the pump 10 for delivery of the solutions.

The following is an exemplary bag configuration:

| Chamber Fill Volumes | |
| --- | --- |
| Chamber 1 | 5–10 mls. |
| Chamber 2 | 100–120 mls. |
| Chamber 3 | 5–10 mls. |
| Chamber 4 | 5 mls. |

Figure 7:
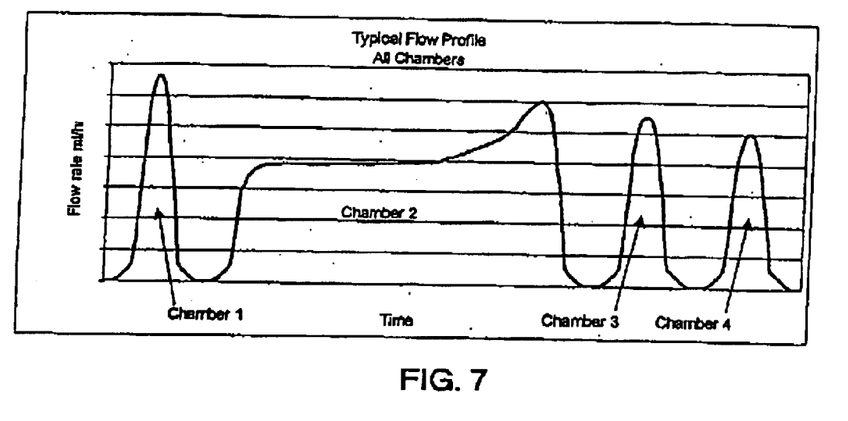
FIG. 7 is a graph showing fluid flow rate, versus time, from chambers 1–4 of a medication delivery bag in accordance with the medication delivery system of the invention.

A typical flow profile of fluid flow from the four bag chambers, versus time, is shown in FIG. 7. The larger chamber 2 has a relatively flat administration profile until the end of the administration where the flow peaks and then rapidly drops to zero. The smaller chambers exhibit peaked administration profiles. The flow rate may be selected by selecting the inner diameter and the length of the micro-bore tubing. A smaller inner diameter or a longer length reduces the flow rate and increases the administration time. Conversely, a larger inner diameter or a short length increases the flow rate and decreases the administration time.

The entire disclosures of U.S. application Ser. No. 09/008,111 and application Ser. No. 09/235,535, both titled "Medication Delivery Apparatus", and of U.S. applications titled "Medication Delivery Container" (further identified by attorney docket number TAND1130), and "Medication Delivery Pump" (further identified by attorney docket number TAND1140), both filed concurrently on the same date as this application, are incorporated herein by reference.

While the invention has been described in detail with reference to certain preferred embodiments thereof, it will be understood that modifications and variations are within the spirit and scope of that which is described and claimed.

What is claimed is:

1. A medication delivery system, comprising:
    a bag,
    an administration set, and
    a pump,
    said bag having:
        at least one chamber containing a medication fluid, and
        a manifold, wherein said manifold comprises at least one back check valve associated with a respective chamber of the bag, wherein a hydraulic lock is formed between the back check valve(s) and the air-eliminating filter of the administration set, which lock is overcome upon the application of a threshold pressure on the chamber;
    said administration set adapted to receive the medication fluid from the bag at a predetermined pressure and deliver the medication fluid to an infusion site at a predetermined flow rate, wherein the administration set includes an air-eliminating filter for eliminating air bubbles from the medication fluid before delivery of the fluid to the infusion site; and
    said pump having an activating mechanism configured to activate said chamber(s) to dispense said fluid from the bag, wherein the activating mechanism generates the predetermined pressure in each chamber.

2. A system according to claim 1, wherein a configuration of the chamber(s) determines the pressure generated therein by the activating mechanism.

3. A system according to claim 1, wherein said activating mechanism comprises a constant force spring.

4. A system according to claim 1, wherein chambers in said bag are activated based on a predetermined configuration of said chambers.

5. A system according to claim 1, wherein the administration set includes a micro-bore tubing having a length and an inner diameter that establishes the predetermined flow rate.

6. A medication delivery system, comprising:
    a bag comprising
        a plurality of chambers and a plurality of bag ports through an outer surface of said bag, each said chamber in fluid communication with at least one said bag port, and
        a manifold assembly comprising a plurality of manifold ports integrally coupled to said bag ports, and at least one common port, whereby each said chamber is in fluid communication with at least one said manifold port to provide a flow path for delivering medications out of said chambers to said common port; and
    a pump having an activating mechanism configured to activate said chambers to dispense said pharmacological agents from said bag.

7. A system according to claim 6, further comprising an administration set that receives the medication fluid from the bag at the predetermined pressure and delivers the medication fluid to an infusion site at a predetermined flow rate.

8. A system according to claim 7, wherein the administration set includes a micro-bore tubing having a length and an inner diameter that establishes the predetermined flow rate.

9. A system according to claim 8, wherein the administration set includes an air-eliminating filter for eliminating air bubbles from the medication fluid before delivery of the fluid to the infusion site.

10. A system according to claim 9, wherein said manifold comprises at least one back check valve associated with a respective chamber of the bag, wherein a hydraulic lock is formed between the back check valves and the air-eliminating filter, which lock is overcome upon the application of a threshold pressure on the chamber.

11. A system according to claim 6, wherein the activating mechanism generates a predetermined pressure in each chamber.

12. A system according to claim 6, wherein a configuration of the chamber(s) determines the pressure generated therein by the activating mechanism.

13. A system according to claim 6, wherein said activating mechanism comprises a constant force spring.

14. A system according to claim 6, wherein chambers in said bag are activated based on a predetermined configuration of said chambers.

15. A medication delivery system, comprising:
    a bag comprising
        a plurality of chambers, a plurality of bag ports through an outer surface of said bag, wherein each said chamber is in fluid communication with at least one said bag port via a conduit, and a plurality of exit ports connecting each said chamber to an associated conduit, wherein said bag is configured and arranged such that each chamber does not overlap with any adjacent chamber along at least one axis of said bag, and said bag ports are positioned substantially perpendicular to said axis along an edge of said bag, and a manifold assembly comprising a plurality of manifold ports and at least one common port, wherein each said chamber is in fluid communication with at least one said manifold port; and a pump having an activating mechanism configured to activate said chambers to dispense said pharmacological agents from said bag, whereby fluid flow within said bag occurs from each said chamber via an associated exit port, an associated conduit, an associated bag port, and an associated manifold port, to said common port.

16. A system according to claim 15, further comprising an administration set that receives the medication fluid from the bag at the predetermined pressure and delivers the medication fluid to an infusion site at a predetermined flow rate.

17. A system according to claim 19, wherein the administration set includes an air-eliminating filter for eliminating air bubbles form the medication fluid before delivery of the fluid to the infusion site.

18. A system according to claim 17, wherein said manifold comprises at least one back check valve associated with a respective chamber of the bag, wherein a hydraulic lock is formed between the back check valves and the air-eliminating filter, which lock is overcome upon the application of a threshold pressure on the chamber.

19. A system according to claim 16, wherein the administration set includes a micro-bore tubing having a length and an inner diameter that establishes the predetermined flow rate.

20. A system according to claim 15, wherein the activating mechanism generates a predetermined pressure in each chamber.

21. A system according to claim 15, wherein a configuration of the chamber(s) determines the pressure generated therein by the activating mechanism.

22. A system according to claim 15, wherein said activating mechanism comprises a constant force spring.

23. A system according to claim 15, wherein chambers in said bag are activated based on a predetermined configuration of said chambers.

24. A medication delivery system, comprising:

a bag comprising a plurality of chambers comprising a plurality of pharmacological agents, each said chamber configured with a respective geometry, wherein said chamber configuration controls the volume of each pharmacological agent administered, the rate at which each pharmacological agent is administered, and the regimen with which said pharmacological agent is administered, and a manifold; and a pump having an activating mechanism configured to activate said chambers to dispense said pharmacological agents from said bag.

25. A system according to claim 24, further comprising an administration set that receives the medication fluid from the bag at the predetermined pressure and delivers the medication fluid to an infusion site at a predetermined flow rate.

26. A system according to claim 25, wherein the administration set includes a micro-bore tubing having a length and an inner diameter that establishes the predetermined flow rate.

27. A system according to claim 26, wherein the administration set includes an air-eliminating filter for eliminating air bubbles from the medication fluid before delivery of the fluid to the infusion site.

28. A system according to claim 24, wherein the activating mechanism generates a predetermined pressure in each chamber.

29. A system according to claim 24, wherein a configuration of the chamber(s) determines the pressure generated therein by the activating mechanism.

30. A system according to claim 24, wherein said activating mechanism comprises a constant force spring.

31. A method for delivering medication fluids, said method comprising:

compressing a bag having at least one chamber containing a medication fluid and a manifold using a constant force spring to generate a predetermined pressure in the chamber based on the chamber's configuration; wherein said manifold comprises at least one back check valve associated with a respective chamber of the bag, and delivering the medication fluid from the bag at the predetermined pressure to an infusion site using an administration set comprising:

micro-bore tubing having a length and an inner diameter that establishes a predetermined flow rate, and an air-eliminating filter, wherein a hydraulic lock is formed between the back check valve(s) of the manifold and the air-eliminating filter, which lock is overcome upon the application of a threshold pressure on the chamber.

\* \* \* \* \*